US006468215B1

United States Patent
Sarvazyan et al.

(10) Patent No.: US 6,468,215 B1
(45) Date of Patent: Oct. 22, 2002

(54) METHOD AND DEVICE FOR MULTI-PARAMETRIC ULTRASONIC ASSESSMENT OF BONE CONDITIONS

(75) Inventors: Armen P. Sarvazyan, Lambertville; Alexej Tatarinov, North Brunswick, both of NJ (US)

(73) Assignee: Artann Laboratories, Lambertville, NJ (US)

( * ) Notice: Subject to any disclaimer, the term of this patent is extended or adjusted under 35 U.S.C. 154(b) by 0 days.

(21) Appl. No.: 09/906,156

(22) Filed: Jul. 16, 2001

(51) Int. Cl.[7] .................................................. A61B 8/00
(52) U.S. Cl. ....................................... 600/438; 600/449
(58) Field of Search ................................ 600/437, 438, 600/442, 449, 586; 73/599, 597, 602

(56) References Cited

U.S. PATENT DOCUMENTS

| | | | |
|---|---|---|---|
| 4,774,959 A | | 10/1988 | Palmer et al. |
| 5,259,384 A | * | 11/1993 | Kaufman et al. ............ 600/437 |
| 5,349,959 A | | 9/1994 | Weiner et al. |
| 5,433,203 A | * | 7/1995 | Kimura et al. .............. 600/442 |
| 5,603,325 A | * | 2/1997 | Mazess et al. .............. 600/442 |
| 5,720,290 A | | 2/1998 | Buhler et al. |
| 5,840,029 A | | 11/1998 | Mazess et al. |
| 5,921,929 A | * | 7/1999 | Goll et al. ................... 600/438 |
| 6,029,078 A | | 2/2000 | Weinstein et al. |
| 6,086,538 A | * | 7/2000 | Jorgensen et al. .......... 600/449 |
| 6,135,964 A | | 10/2000 | Barry et al. |
| 6,213,958 B1 | * | 4/2001 | Winder ....................... 600/586 |

* cited by examiner

Primary Examiner—Marvin M. Lateef
Assistant Examiner—Ali M. Imam
(74) Attorney, Agent, or Firm—Mathews, Collins, Shepherd & McKay, P.A.

(57) ABSTRACT

A method of assessment of bone conditions comprises acquiring of unilateral sequential ultrasonic measurements along the trajectory over the surface of an examined bone. The method utilizes measurements of a set of ultrasonic parameters from a plurality of ultrasonic transfucers moved along the tested bone surface. Measured parameters are displayed as profile graphs characterizing bone conditions. The set of measured and displayed ultrasonic parameters can include: velocity of a longitudinal wave; velocity of a flexural wave; attenuation of the longitudinal wave; attenuation of the flexural wave; frequency slope of attenuation of the longitudinal wave; frequency slope of attenuation of the flexural wave; changes of spectral characteristics of propagating the longitudinal wave; and changes of spectral characteristics of propagating the flexural wave. To eliminate the influence of soft tissues on the measured parameters, the thickness of soft tissue layer over the examined area of bone is measured by pulse-echo ultrasonic channels incorporated in the transducers. Based on the ultrasound parameters and their combinations, quantitative evaluation of bone mineralization (ossification) status, structure and cortical thickness is made. The method of the present invention comprises a multi-transducer probe, tools for controlling the pressure with which the transducers contact the skin surface, and a digital counter measuring the distance traveled by the probe along the predetermined trajectory on the examined bone surface.

23 Claims, 5 Drawing Sheets

METHOD AND DEVICE FOR MULTI-PARAMETRIC ULTRASONIC ASSESSMENT OF BONE CONDITIONS

This invention was made with government support under NIH grants 1 R43 AG17400-01 and 1 R43 AR 46662-01 awarded by the National Institutes of Health, National Cancer Institute. The government has certain rights in this invention.

BACKGROUND OF THE INVENTION

1. Field of the Invention

The present invention corresponds to a method and device for quantitative evaluation of status of bones implying assessment of bone mechanical properties, mineralization (ossification), porosity and fracture risk, and detection of local lesions.

2. Description of Related Art

The importance of assessment of bone quality is mainly related to the necessity for diagnostics of osteoporosis. Osteoporosis presents a common public health problem becoming increasingly important as population ages, affecting a large proportion of post-menopausal women and senile people of both genders. Secondary osteoporosis and complicated osteopenia are factors inherent to a variety of metabolic and endocrine disorders that require monitoring during treatment of the primary disease. Monitoring of skeletal growth and maturation is a measure to assess in general healthy development of children and adolescents by right nutrition and sufficient exercise that is of critical importance in the formation of strong musculoskeletal systems and in preventing osteoporosis later in life. The pediatric application strongly demands accounting the growth process.

Conventional means of bone quality diagnostics include radiography and planar X-ray which are usually applied in orthopedics for visualization of bone lesions, deformities, displacements, etc. Roentgenography is traditionally applied to determine the degree of ossification and synostosis for assessment of skeletal age and clearly shows clinical manifestations of osteoporosis like vertebral compressions at the developed stage. Although relatively insensitive for detection of osteopenia and examination of mineral content, the conventional radiography detects bone loss only when it achieves 30–40%.

Widely applied for assessment of postmenopausal and senile osteoporosis, radiological densitometers include families of whole body and peripheral scanners, utilizing single- and dual-energy photon apsorptiometry (SPA, DPA), dual-energy x-ray absorption (DXA), and peripheral quantitative computed tomography (pQCT). The main advantage of these instruments is their ability to measure bone mass, bone mineral content and bone mineral density with high precision and to access the most responsive sites such as the spine and hip. The pQCT provides measurements of both the cross-section size and density of the bone without influence from the overall body size that is particularly important for the evaluation of bone resorption during osteoporosis and accumulation of bone mass in growing bones of children. Unfortunately, there are multiple reasons, which include high cost, lack of portability and hazardous radiation exposure, that limit availability of this technique encumbering its use in wider screening and monitoring of the at-risk population. In addition, volumetric measurements of bone substance by radiation absorption do not reveal changes in mechanical and micro-structural properties associated with bone toughness and brittleness that are other factors of bone fracture risk.

Quantitative ultrasound (QUS) presents an alternative to the x-ray densitometry, based on measurement of parameters of propagation of elastic waves through bone and interaction of the waves with bone substance. The ultrasound parameters, including velocity of ultrasound and frequency slope of attenuation, relate to elastic mechanical properties and structure of in vivo bone. The ultrasonometers present several advantages, such as: (1) provision of information on the elastic properties and structural changes (porosity) of bone, which is not accessible by DXA; (2) no irradiation hazard, allowing radiation-safe and off-repeated measurements; (3) portability, ease of use, and lower costs. The QUS devices are highly specialized in relation to application and are classified as sonometers for heel, phalanx, tibia and multi-site testing devices.

Conventional solutions have included proposing different modifications of ultrasound bone analyzers, applying pulse transition methods to heel bone and varied approaches for transducers application and signal processing. For example, U.S. Pat. No. 4,774,959 describes a narrow band ultrasonic frequency attenuation bone measuring system. U.S. Pat. No. 5,349,959 describes an ultrasonic densitometer device and method. U.S. Pat. No. 5,720,290 relates to an apparatus and method for acoustic analysis of bone using optimized functions of spectral and temporal signal components. Introduction of a number of transducer locations and bone imaging through the scanning procedure allowed to increase precision of diagnostics by direct detection of "region of interest", being important due to bone spatial heterogeneity, as described in U.S. Pat. No. 5,840,029 of an imaging ultrasonic densitometer and U.S. Pat. No. 6,086,538 of a method and apparatus for evaluation of bone condition. Other recent attempts to increase reliability of diagnostics were aimed to create a united systems incorporating an ultrasonometer and biomarkers, as described in U.S. Pat. No. 6,029,078 as a system for assessing bone characteristics, and to increase accuracy by multiple contact applications, as described in U.S. Pat. No. 6,135,964 as an ultrasonic bone testing apparatus with repeatable positioning and repeatable coupling. The conventional QUS techniques for long bones utilize a relatively simplified recording of ultrasound velocity at cross-bone or along-bone propagation influenced by both bone geometrical and material properties and present no information about their separate contribution. The following limitations of conventional QUS are found.

1) There is a numerical superiority of heel QUS techniques over long bone QUS, allowing good opportunity to evaluate density of trabecular structure in osteoporosis, but limiting QUS application for other sites of the skeleton, thereby hampering comprehensive evaluation of osteoporosis and monitoring of bone growth and ossification during childhood;
2) Existing long bones QUS obtain non-specified integral data on changes of bone geometrical (cortical thickness), material (stiffness, mineralization) and structural (porosity) properties.
3) The conventional QUS devices for long bones do not provide a scanning option, capable of presenting spatial characteristics of bone growth, ossification and atrophy.

SUMMARY OF THE INVENTION

The present invention relates to a method of assessment of bone condition in which a probe takes unilateral sequential ultrasonic measurements along a trajectory of the bone. The probe includes emitting and receiving transducers. Ultrasound propagation parameters can be calculated from ultrasonic signals received at the receiving transducer and distance readings acquired along the trajectory. The set of measured and displayed ultrasonic parameters can include: velocity of a longitudinal wave; velocity of a flexural wave; attenuation of the longitudinal wave; attenuation of the flexural wave; frequency slope of attenuation of the longitudinal wave; frequency slope of attenuation of the flexural wave; changes of spectral characteristics of propagating the longitudinal wave; and changes of spectral characteristics of propagating the flexural wave. The ultrasound propagation parameters can be evaluated for determining characteristics of the bone.

The present invention for the method and device for multi-parametric ultrasonic assessment of bone conditions has the advantages of: 1) the ability to scan examined trajectory along bone and to present spatial distribution of ultrasonic parameters; and, 2) to examine bone by different ultrasonic wave modes (longitudinal and flexural) and on variable ultrasonic frequencies and to extract comprehensive parameters illustrative on the elastic, geometrical and structural properties of bone. Clinical benefits provided by the present invention are listed below.

1. Measurements of velocity of a flexural wave provide an opportunity to determine cortical thickness of bone. The cortical thickness of bone can be used to estimate the degree of resorption during osteoporosis, usually progressing from the bone channel, as well as to evaluate the accumulation of bone mass in children and adolescents during skeletal growth.
2. Measurements of velocity of a longitudinal wave can be used to evaluate the elastic properties of the bone matrix sensitive to accumulation of micro-defects during osteoporosis and to the level of osteoid mineralization during bone development.
3. The combined stiffness index from the flexural and longitudinal velocities provides information about the total mechanical endurance of bone and its capacity to withstand loading.
4. The frequency slope of attenuation combined with derivatives of signal spectrum form a bone structural index, sensitive to changes of porosity and size of structural components, presence of voids and spatial defects.
5. Longitudinal profiles of ultrasonic parameters provide valuable information on spatial distribution of bone characteristics. This permits the estimation of the stage of atrophy expansion along the bone that usually initiates in the epiphyseal and metaphyseal area of long bones during osteoporosis, continuously involving a larger area toward the diaphysis. As for the pediatric application, the longitudinal profiles can be used to monitor bone growth area and to determine bone ossification status, as well as skeletal age by cessation of growth zones.
6. Detection of local weakness areas like cysts or poorly consolidated fractures and determination of spatial length of the areas can be carried out through analysis of the longitudinal profiles.
7. The exclusion of soft tissues influence by introducing an auxiliary pulse-echo mode provides increased accuracy of measurements and makes possible examination of skeletal areas under thicker soft tissue layers.
8. The automatic determination of a "region of interest" by processing of the longitudinal profiles provides a reliable reference to anatomical landmarks of bone in order to obtain comparable data.

The invention will be more fully described by reference to the following drawings.

DETAILED DESCRIPTION

Figure 1:
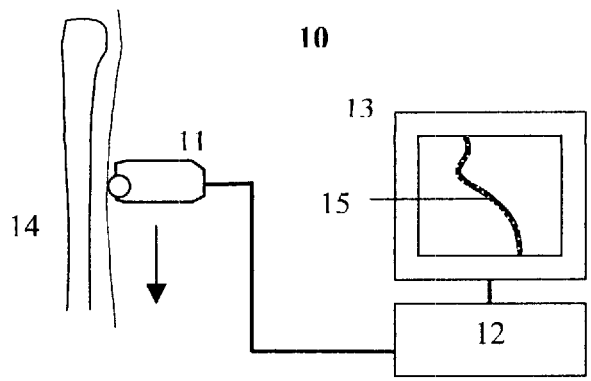
FIG. 1 is a schematic diagram showing the general structure of the device of the present invention, comprising an ultrasonic manual scanning probe, data acquisition electronic circuit, and data processing and display unit.

Reference will now be made in greater detail to a preferred embodiment of the invention, an example of which is illustrated in the accompanying drawings. Wherever possible, the same reference numerals will be used throughout the drawings and the description to refer to the same or like parts.

FIG. 1 is a schematic diagram of the device for quantitative and non-invasive assessment of bone conditions in accordance with device 10, comprising ultrasonic manual scanning probe 11, data acquisition electronic circuit 12, and data processing and display unit 13. Probe 11 is pressed against bone 14 covered by skin 16 and a layer of underlying-soft tissue 21. During the examination, the operator moves probe 11 along bone 14 slightly pressing probe 11 against skin 16. Examination results are presented on display unit 13, for example as profile graphs of ultrasonic parameters and derivative diagnostic indexes 15 along the examined bone 14.

Figure 2:
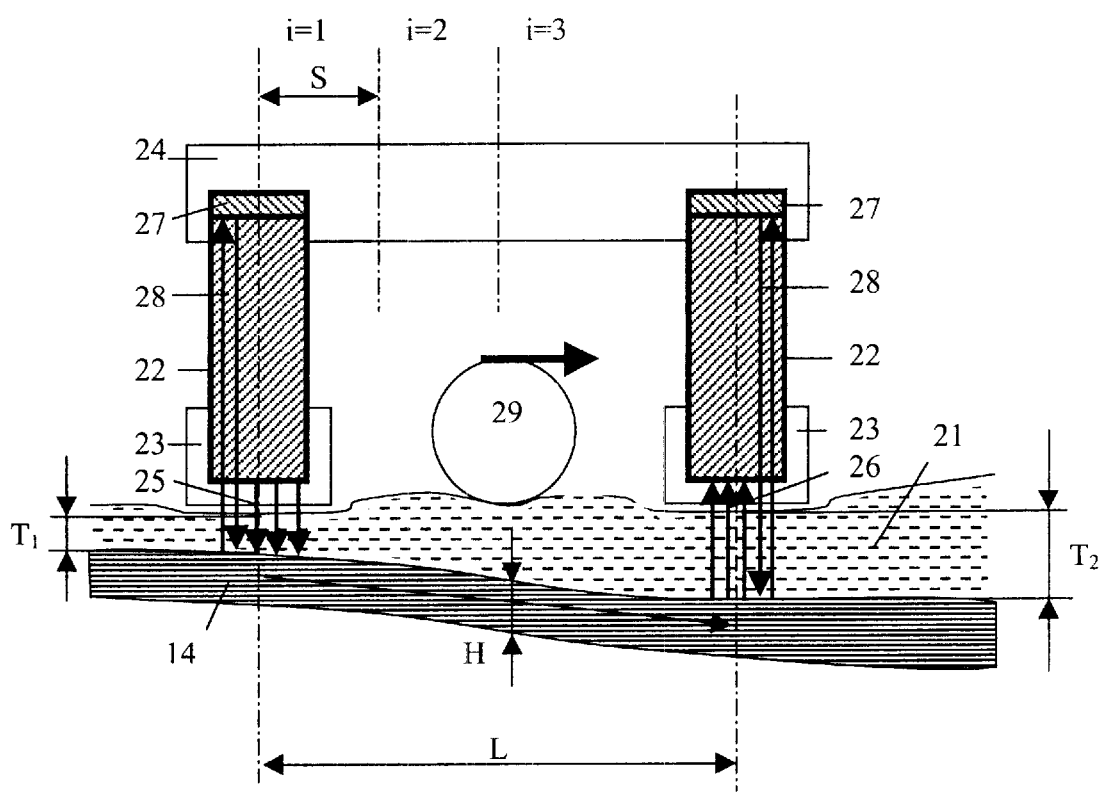
FIG. 2 is a schematic diagram illustrating the method of multi-parametric ultrasonic bone testing of the present invention as applied to the bone surface covered by a soft tissue layer.

The proposed ultrasonic method of the present invention is depicted in FIG. 2. Bone 14 covered by a layer of soft tissues 21 is tested with a pair of ultrasonic transducers 22 of probe 11 working in pulse transmission mode and contacting with skin 16 through wave-guiding contact tips 23. One of transducers 22 is an emitter and a second one of transducers 22 is a receiver of ultrasonic waves propagated along bone 14. Transducers 22 are fixed on a rigid frame 24 to provide a constant base for measurements of ultrasound propagation parameters in the pulse transmission mode. Base length L is chosen on the basis of a trade off between reliable detection of ultrasound propagation velocities of longitudinal and flexural wave components and spatial resolution of profiles 15. To acquire multiple ultrasonic parameters for different types of waves and broadband spectral characteristics, a plurality of multiplexed ultrasound signals 25 with different frequencies are excited from the emitting transducers 22, and ultrasonic responses 26 are detected by the receiving transducers 22. For forming multi-frequency signals 25 and 26, transducers 22 comprise piezotransducers, selectively activated by a predefined multiplexing algorithm. By processing ultrasonic signals 26, the ultrasonic parameters of bone 14 reflecting bone mechanical properties, structure and average cortical thickness H along the bone are estimated.

It has been found that accuracy of measurements of ultrasonic parameters of the bone can be significantly affected by the contribution of layer of soft tissue 21 which may vary in thickness, unevenly depending on a patient's constitution and anatomical region peculiarities. To eliminate the contribution of the soft tissue layer, pulse-echo channels for thickness measurements are included in probe 11. High frequency piezotransdusers 27 can be mounted on both transducers 22 to provide generation and reception of short ultrasonic pulses 28 propagating towards the bone 14 and reflected from its surface. Time delays $T_1$ and $T_2$ are measured, and thickness of layer of soft tissue 21 under both transducers 22 is calculated for further accounting during calculation of ultrasonic parameters in bone 14. Starting at the initial point of examined region of the bone 14 (i=1), the measurements are discretely repeated during continuous probe movement performed by the operator along bone 14. Accordingly, a series of ultrasonic signals is accumulated at numerous points along bone 14 (i=2, 3 . . . n) with step S. The distance of the passed trajectory is controlled by distance meter 29. Discrete distance readings are acquired simultaneously with ultrasonic measurements to form longitudinal profile graphs 15.

Figure 3:
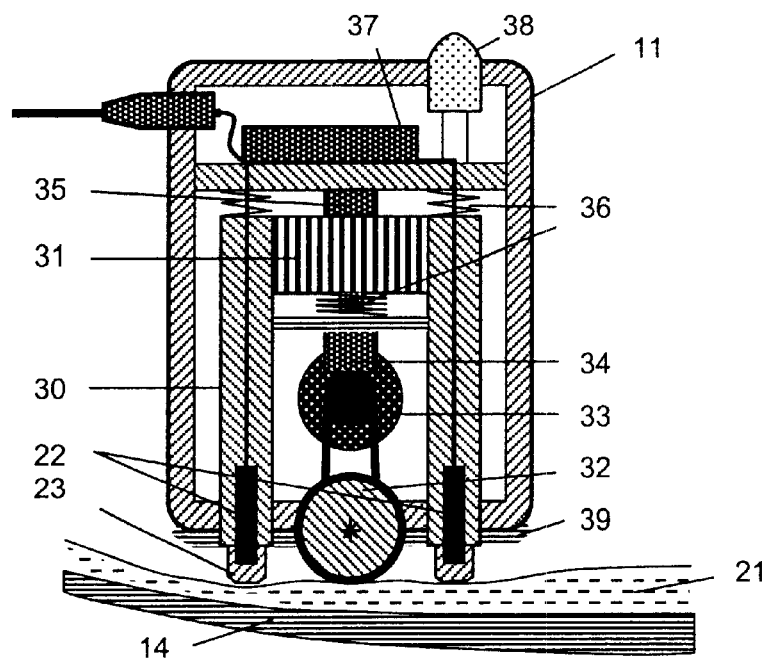
FIG. 3 is a cross-sectional view of an ultrasonic probe for manual scanning with acoustical, mechanical and electronic components.

FIG. 3 illustrates schematically the structure of probe 11. Probe 11 has a two-point acoustical contact with bone 14 through layer of soft tissues 21 and touches skin 16 with contact tips 23. The composite ultrasonic transducers 22 are mounted on a support 30. Support 30 and an intermediate base element 31 form a rigid base. Sufficient length of support 30 and sound-absorbing structure of base element 31 facilitate elimination of ultrasonic feed-through disturbances. Distance meter 29 comprises a rolling wheel 32 contacting the patient's skin 16 and rotating during movement of probe 11. Perforated counter wheel 33 is connected to rolling wheel 32 with a transmission. Optical pulse counter 34 counts the number of pulses corresponding to discrete steps of rotation of rolling wheels 32 and a perforated counter wheel 33. The number of the counted pulses correlates to the distance passed by probe 11. Pressure sensor 35 controls sufficiency of contact pressure on probe 11 with the patient's body. Uniformity of contact pressure under both transducers 22 and secure contact of rolling wheel 32 with skin 16 is achieved using spring elements 36. Microcontroller 37, incorporated in probe 11, manages pressure sensor 35, optical pulse counter 34 of distance meter and light diode 38. Distance meter and light diode 38 indicate adequate pressure level on the probe 11 during manual scanning. Protection plate 39 provides isolation of internal parts of probe 11.

Figure 4:
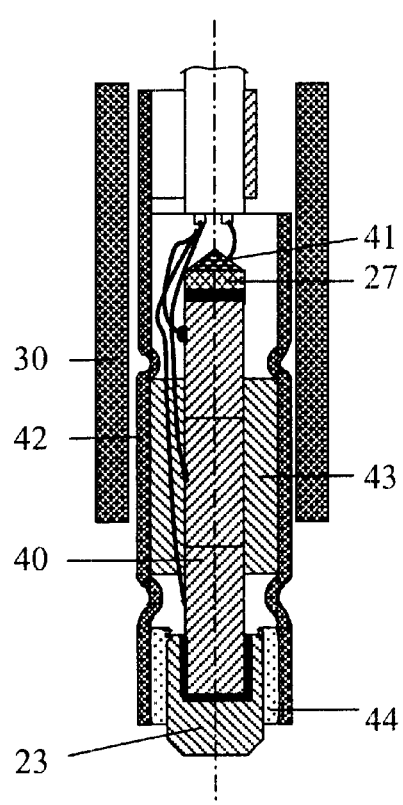
FIG. 4 is a schematic illustration of structure of an ultrasonic transducer, comprising a multi-frequency transducer for bone examination and pulse-echo transducer for measuring soft tissue thickness.

FIG. 4 is a schematic illustration of the structure of ultrasonic transducer 22. Piezotransducer 40 emits and receives ultrasound by the surface adjacent to the patient's body. To provide a series of signals differing by spectral composition, a plurality of harmonics of piezotransducer 40 are used. The series of signals can be achieved by switching of voltage of changed polarity to separate parts of piezotransducer 40 according to a predefined multiplexing algorithm. The range of ultrasound frequencies used is from 70 kHz to 700 kHz to provide a sufficiently wide bandwidth of ultrasound wavelength to the cortical thickness H ratio. Contact tip 23 can be made of a hard plastic to assure easy cleaning, good acoustic coupling with skin 16 and minimum friction without use of an additional lubrication during probe movement. Pulse-echo piezotransducer 27 for measuring thickness of the soft tissue layer 21 is mounted on the upper end of piezotransducer 40. Piezotransducer 40 serves as a buffer acoustical wave-guide. To precisely measure ultrasound delay in the soft tissues layer 21, pulse-echo piezotransducer 27 produces short ultrasonic pulses of about 1 mks with carrier frequency of about 3–4 MHz emitted by pulse echo piezotransducer 27 with acoustical damping prism 41. Housing 42 provides mechanical protection and electrical screening of ultrasonic transducers 22 and pulse echo piezotransducer 27. Piezotransducer 40 can be fixed in housing 42 using polymer gaskets 43 and 44. Polymer gaskets 43 and 44 also serve as electrical isolators.

Figure 5:
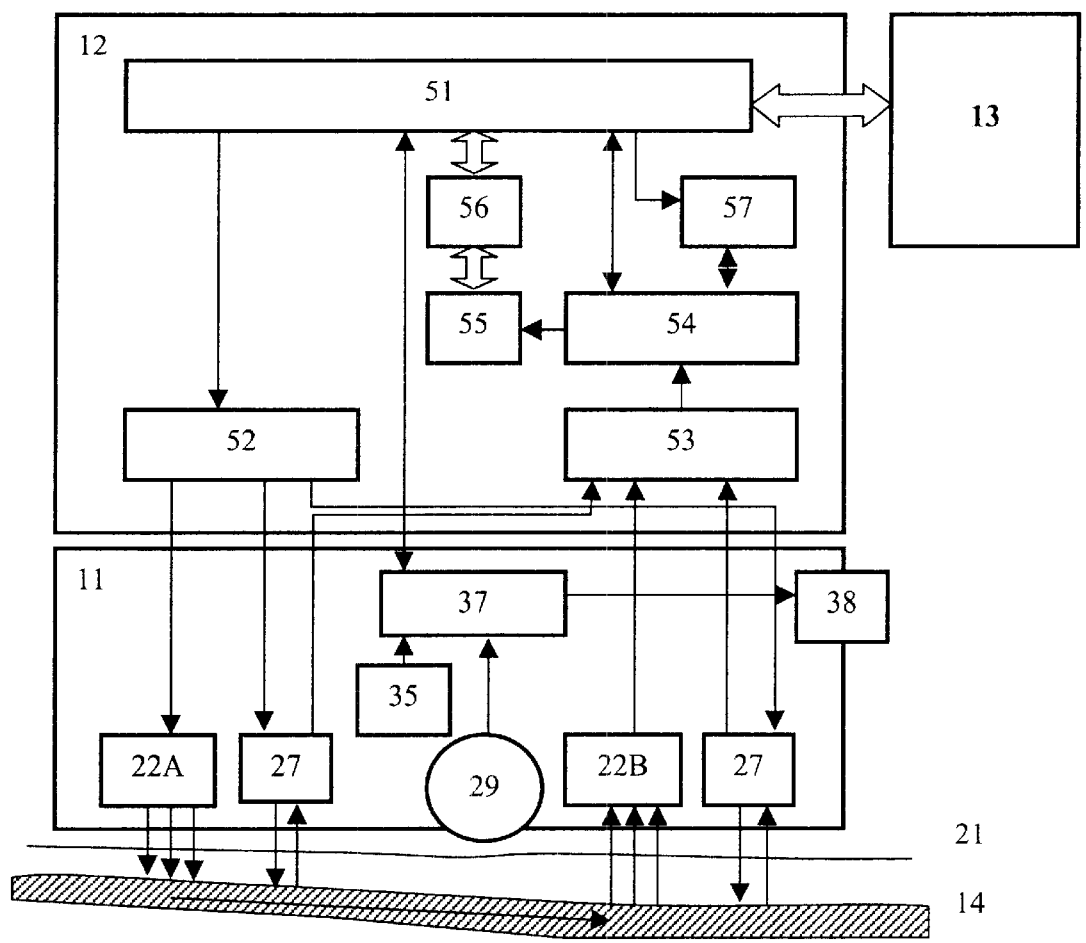
FIG. 5 is functional block diagram of the device of the present invention.

FIG. 5 depicts a functional scheme of device 10. Functional elements of ultrasonic probe 11 include: ultrasonic transducers 22A and 22B for bone 14 examination in pulse propagation mode; piezotransducers 27 for measuring thickness of soft tissues layer 21 in pulse-echo mode; distance meter 29; pressure sensor 35; microcontroller 37 for managing distance meter 29 and pressure sensor 35; and light diode 38 as a contact indicator of probe 11 with the patient's body. Integrated peripheral controller 51 is a central processor for data acquisition electronic unit 12 performing main control functions, such as management of multiplexing of output and input ultrasonic channels, readings from distance meter 29, primary processing of ultrasonic signals and data transfer to data processing and display unit 13. High voltage drivers 52 activate in turn emitting ultrasonic transducer 22A and pulse-echo piezotransducers 27, with the switch order being set by software algorithms of controller 51. Acquired ultrasonic signals from ultrasonic transducer 22B and pulse-echo piezotransducer 27 are amplified by a cascade of input amplifiers 53, digitized by fast ADC 55 according to the order established by multiplexer 54, and collected in buffer RAM 56. DAC 57 serves for managing the gain of input amplifiers 53. The device 10 is capable to perform in real time the processing of ultrasonic signals and control functions, including comparison of averaged signal arrays and multiplexing of measurement modes. Fast data exchange between data processing unit 13 and data acquisition electronic unit 12 provides data processing and displaying in real time during the procedure of manual scanning.

Figure 6:
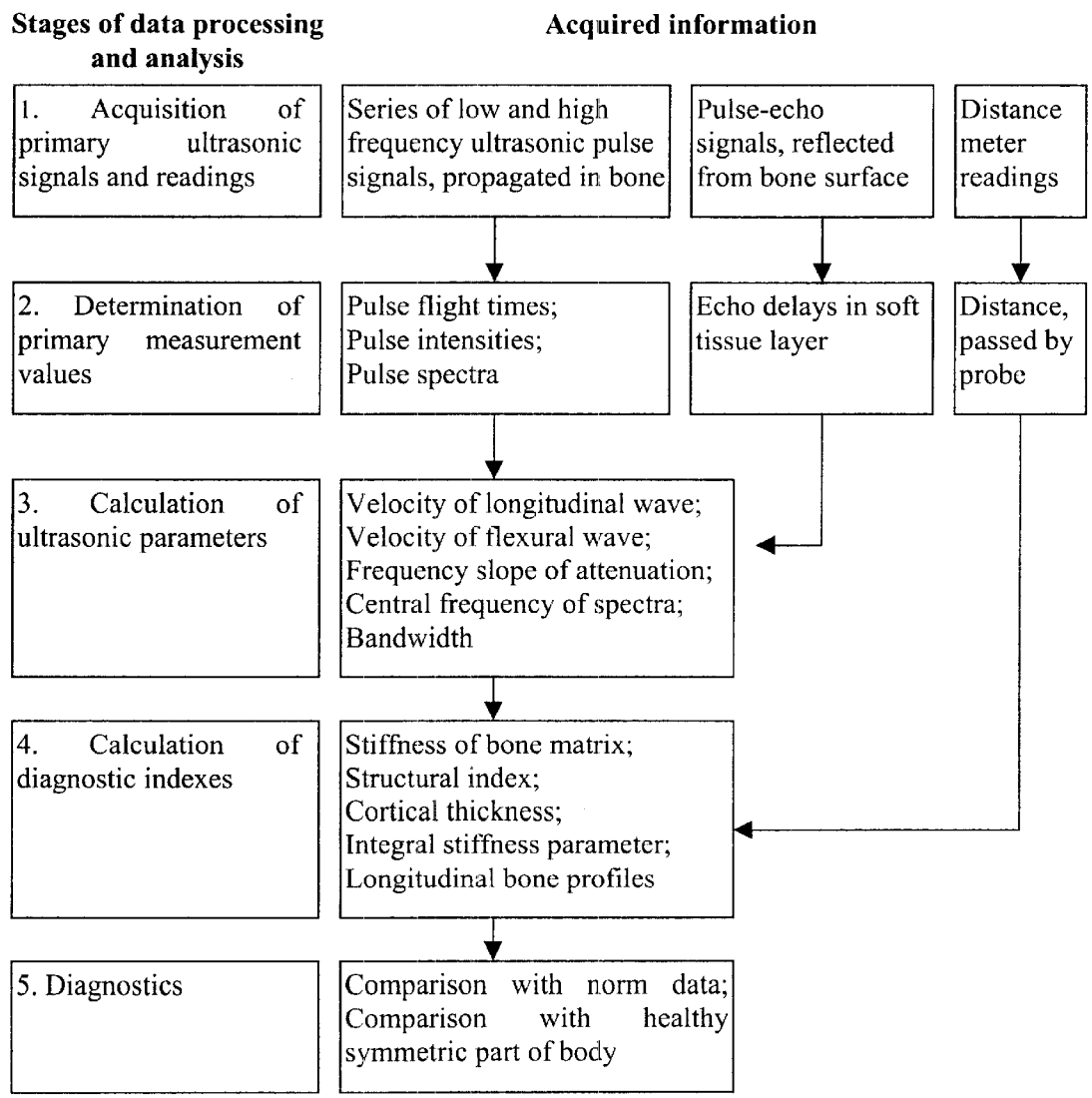
FIG. 6 is a schematic flow diagram illustrating steps of data processing, acquiring information and determining diagnostic parameters.

Stages of data processing and determination of diagnostic parameters are shown in FIG. 6. In stage 1, ultrasonic signals from transducers 22 and pulse-echo piezotransducer 27 are digitized and transferred to data processing unit 13 simultaneously with readings of distance meter 29. In stage 2, pulse flight times are determined by relative amplitude levels of the pulse front arrivals, characteristic points of pulses shape or relative energetic levels. Pulse intensities are determined as amplitude integrals in certain time intervals, starting from pulse front arrivals. For example, pulse spectra can be determined by Fourier transform. In stage 3, ultrasound velocities are calculated from the pulse flight time measurement in bone 14 adjusted by time delays in soft tissue layer 21. Velocity of the ultrasonic longitudinal wave is determined using high frequency signals traveling along the surface of bone 14. Velocity of the flexural wave is determined by low frequency signals with the wavelength of ultrasound exceeding the cortical thickness H. Frequency slope of attenuation is a function of decrease of the signal intensity with increasing frequency and is determined from a comparison of signals obtained on different harmonics of transducers 22 or from the pulses spectra. Central frequency of pulse spectra is determined as an integral center in a preset frequency range. Spectral bandwidth characterizes the range of frequencies of received signals. Diagnostic indexes are derivatives of single or combined ultrasonic parameters. In Stage 4, stiffness of bone matrix is determined as a derivative of the longitudinal wave velocity, correlating with the elasticity modulus. Structural index as an indicator of porosity is a parameter composed of frequency slope of attenuation, shift of central frequency and bandwidth of ultrasonic spectra. Cortical thickness H is determined from the correlation function of dependence between the thickness and flexural wave velocity. Integral stiffness of the bone cortex, which is related to both the stiffness of bone matrix and cortical thickness, is defined by algebraic combination of velocities of longitudinal and flexural waves. Longitudinal profile graphs 15 are final presentations of the diagnostic indexes distributed along examined plot of bone 14. In stage 5, diagnostic decision about bone condition and presence of local lesions is determined on the basis of comparison of the diagnostic indexes profile graphs 15 with the normal graphs for the particular gender and age or by comparing with a presumably healthy symmetrical region.

Figure 7:
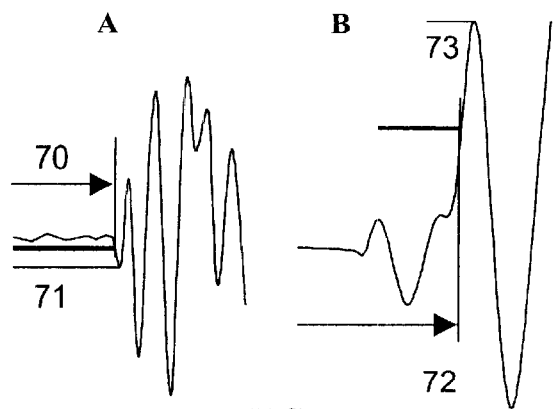
FIG. 7 is a graph illustrating the principle of measurement of pulse flight times for determination of velocities of longitudinal and flexural ultrasonic waves.

FIG. 7 illustrates a principle of measurement of pulse flight times for determination of ultrasound velocities related to the longitudinal (A) and flexural (B) waves. The longitudinal wave velocity in bone 14 is determined at higher frequencies of ultrasound emitted by transducers 22, typically in the range about 200–500 kHz to avoid expressed influence of geometrical dispersion. The pulse flight time 70 is measured at certain amplitude level of the received signal relative to the amplitude of the first peak 71. The flexural wave velocity is defined at lower frequencies produced by transducer 22, typically in the range of 60–200 kHz. In this case, the wavelength of ultrasound several times exceeds cortical thickness H, and the phenomenon of geometrical dispersion is effectively exploited to determine cortical thickness H based on the relationship between the thickness and the flexural wave velocity. Pulse flight time 72 is measured at certain amplitude level related to first characteristic peak 73 that several times exceeds amplitude of the earlier arriving longitudinal wave.

Figure 8:
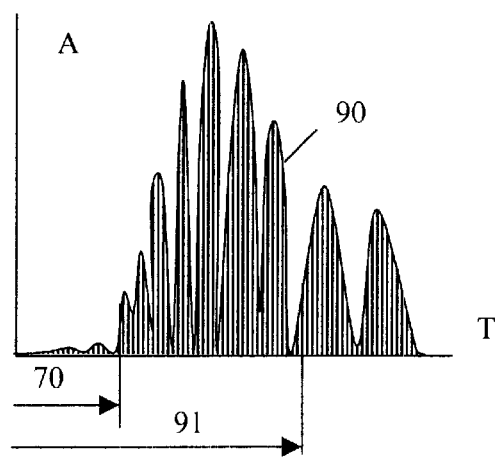
FIG. 8 illustrates the principle of measurement of intensity of ultrasonic pulse.

FIG. 8 illustrates a principle of measurement of intensity of ultrasonic pulse for calculating the frequency slope of attenuation. Digitized ultrasonic signals are rectified. Intensity is determined as integral area of rectified signal 90 between pulse flight time 70 and some pre-set time interval 91.

Figure 9:
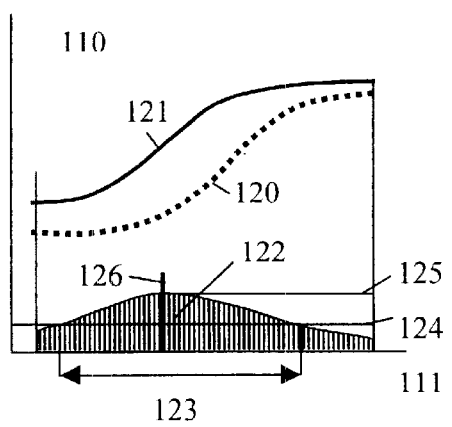
FIG. 9 illustrates diagnostic criteria based on analysis of ultrasonic profile graph along the examined bone.

FIG. 9 illustrates diagnostics of bone condition made by comparison of individual profile graph 120 of diagnostic index 110 along the bone length 111 with the corresponding statistical norm graph 121. The diagnostic values include: integral difference 122; length of weak area 123 that differs from the norm by more than a predetermined threshold 124; peak difference 125 and its location along the bone 126.

It is to be understood that the above-described embodiments are illustrative of only a few of the many possible specific embodiments which can represent applications of the principles of the invention. Numerous and various other arrangements can be readily devised in accordance with these principles by those skilled in the art without departing from the spirit and scope of the invention.

What we claim is:

1. A method for quantitative and non-invasive assessment of bone conditions comprising the steps of:
   acoustical coupling of an ultrasonic probe with a body surface over the bone, said probe comprising emitting and receiving transducers;
   emitting and propagating ultrasonic pulses along a predetermined trajectory on a surface of said bone with said emitting transducers;
   acquiring a series of ultrasonic signals from said receiving transducers during continuous movement of said ultrasonic probe along said trajectory;
   acquiring distance readings along said trajectory;
   calculating one or more parameters of ultrasound propagation selected from the group consisting of velocities of longitudinal and flexural wave components, attenuation, frequency slope of attenuation, spectral derivatives, and spatial characteristics of said parameters; and
   evaluating said parameters for diagnostically determining characteristics of said bone.

2. The method according to claim 1 wherein the said step of calculating one or more parameters of ultrasound propagation includes elimination of influence of a soft tissue layer over said bone.

3. The method according to claim 2 wherein said elimination of influence of the soft tissue layer is determined by acquiring pulse-echo signals reflected from said surface of said bone to measure thickness of the soft tissue layer under said emitting and receiving transducers.

4. A method for quantitative and non-invasive assessment of bone conditions comprising the steps of:
   acoustical coupling of an ultrasonic probe, with a body surface over the bone, said probe comprising emitting and receiving transducers;
   emitting and propagating ultrasonic pulses along a predetermined trajectory on a surface of said bone with said emitting transducers;
   acquiring a series of ultrasonic signals from said receiving transducers during continuous movement of said ultrasonic probe along said trajectory;
   acquiring distance readings along said trajectory;
   calculating parameters of ultrasound propagation with velocities of longitudinal and flexural wave components, attenuation, frequency slope of attenuation, spectral derivatives, and spatial characteristics of said parameters; and
   evaluating said parameters for diagnostically determining characteristics of said bone,
   wherein the evaluating step further comprises:
   calculating derivative indexes of skeletal status selected from the group of stiffness of bone matrix, thickness of cortex, structural index and integral stiffness on a basis of correlation with the calculated ultrasound propagation parameters or their algebraic combinations; and
   evaluating and displaying spatial profiles of said calculated ultrasound propagation parameters and indexes along the bone.

5. The method according to claim 4 wherein said thickness of cortex of said bone is determined from a predetermined correlation with said velocity of flexural wave component.

6. The method according to claim 4 wherein said stiffness of bone matrix is determined from predetermined correlation with said velocity of said longitudinal wave component.

7. The method according to claim 4 wherein said structural index is determined from algebraic combination of said frequency slope of attenuation and said spectral derivatives.

8. The method according to claim 4 wherein said integral stiffness is determined from algebraic combination of said thickness of the cortex and said stiffness of bone matrix.

9. The method according to claim 1 further comprising the step of; monitoring of contact stability during said emitting and propagation of ultrasonic pulses performed by measuring the pulse flight time and intensity in a series of repeated ultrasonic signals.

10. The method according to claim 1 wherein said parameters of ultrasonic propagation are determined from a series of multi-frequency ultrasonic signals.

11. The method according to claim 10 wherein said multi-frequency ultrasonic signals are obtained by exciting said emitting transducers on different resonant frequencies.

12. The method of claim 1 wherein the step of calculating one or more parameters of ultrasound propagation comprises the parameters of velocities of longitudinal and flexural wave components.

13. The method according to claim 12 wherein said parameters of ultrasonic propagation are determined from a plurality of multi-frequency ultrasonic signals.

14. The method according to claim 13 wherein said multi-frequency ultrasonic signals are obtained by exciting said emitting transducers on different resonant frequencies.

15. The method of claim 13 wherein said velocity of said longitudinal wave component is determined with said ultrasonic pulse in a frequency range of about 200–500 kHz and said velocity of said flexural wave component is determined with said ultrasonic pulse in a range of about 60–200 kHz.

16. The method of claim 12 wherein the step of calculating one or more parameters of ultrasound propagation comprises the parameters of frequency slope of attenuation and spectral derivatives for providing multiparametric characterization of the bone.

17. A method for quantitative and non-invasive assessment of bone conditions comprising the steps of:

acoustical coupling of an ultrasonic probe, with a body surface over the bone, said probe comprising emitting and receiving transducers;

emitting and propagating ultrasonic pulses along a pre-determined trajectory on a surface of said bone with said emitting transducers;

acquiring a series of ultrasonic signals from said receiving transducers during continuous movement of said ultrasonic probe along said trajectory;

acquiring distance readings along said trajectory;

calculating parameters of ultrasound propagation with velocities of longitudinal and flexural wave components, attenuation, frequency slope of attenuation, spectral derivatives, and spatial characteristics of said parameters; and evaluating said parameters for diagnostically determining characteristics of said bone, wherein said evaluating said parameters for diagnostically determining characteristics of said bone is made by comparison of said spatial characteristics of a spatial profile with a statistical norm profile, determined from the group consisting of: analysis of integral difference along the trajectory over said bone; the length of bone area differing from the norm by more than a predetermined threshold; peak difference and spatial location of abnormal area.

18. An apparatus for quantitative and non-invasive assessment of bone conditions comprising:

a probe for scanning along a surface of said bone, said probe comprising multi-frequency emitting and receiving ultrasonic transducers and a distance meter;

processor means for providing acquisition of ultrasonic signals from said receiving ultrasonic transducers;

means for calculating at least one parameter selected from the group consisting of ultrasound velocities of longitudinal and flexural wave components, attenuation, frequency slope of attenuation, and spectral derivatives; and means for displaying spatial profiles of said parameters along a length of said bone.

19. The apparatus according to claim 18 wherein contact pressure of said apparatus with a surface of a body above said surface of said bone is controlled by an electromechanical arrangement.

20. The apparatus according claim 18, wherein said multi-frequency transducer emitting and receiving transducers are a single transducer excited on a plurality of harmonics.

21. The apparatus according claim 18, wherein said multi-frequency transducer emitting and receiving ultrasonic transducers are a complex transducer, comprising a plurality of elements with different resonant frequencies.

22. The apparatus according claim 18 wherein thickness of soft tissues layer above said bone is measured by ultrasonic pulse-echo elements in said ultrasonic transducer.

23. The apparatus according claim 18 wherein said distance meter comprises a rolling wheel, contacting said body surface and means for measurement of rotation of said rolling wheel.

* * * * *